(12) United States Patent
Roxhed et al.

(10) Patent No.: US 10,525,239 B2
(45) Date of Patent: Jan. 7, 2020

(54) CEREBROSPINAL FLUID SHUNT FOR TREATMENT OF HYDROCEPHALUS

(71) Applicants: Niclas Roxhed, Bromma (SE); Staffan Johansson, Bro (SE); Göran Stemme, Lidingö (SE); Anders Eklund, Umeå (SE); Jan Malm, Umeå (SE)

(72) Inventors: Niclas Roxhed, Bromma (SE); Staffan Johansson, Bro (SE); Göran Stemme, Lidingö (SE); Anders Eklund, Umeå (SE); Jan Malm, Umeå (SE)

(*) Notice: Subject to any disclaimer, the term of this patent is extended or adjusted under 35 U.S.C. 154(b) by 882 days.

(21) Appl. No.: 14/673,993

(22) Filed: Mar. 31, 2015

(65) Prior Publication Data
US 2015/0217095 A1 Aug. 6, 2015

Related U.S. Application Data

(63) Continuation of application No. PCT/SE2013/051140, filed on Oct. 1, 2013.

(30) Foreign Application Priority Data

Oct. 1, 2012 (SE) .................... 1200588-0

(51) Int. Cl.
*A61M 27/00* (2006.01)
*F16K 99/00* (2006.01)

(52) U.S. Cl.
CPC ....... *A61M 27/006* (2013.01); *F16K 99/0015* (2013.01); *F16K 99/0059* (2013.01); *F16K 2099/008* (2013.01); *F16K 2099/0088* (2013.01)

(58) Field of Classification Search
CPC .............. A61M 27/006; A61F 9/00781; F16K 99/0015; F16K 99/0059; F16K 2099/008; F16K 2099/0088
(Continued)

(56) References Cited

U.S. PATENT DOCUMENTS 3,886,948 A 6/1975 Hakim
9,381,331 B2 * 7/2016 Seaver ................ A61M 27/006
(Continued)

FOREIGN PATENT DOCUMENTS

DE 10100070 A1 7/2002
DE 10317308 A1 11/2004
(Continued)

OTHER PUBLICATIONS

A MEMS-based passive hydrocephalus shunt for body position controlled intracranial pressure regulation Staffan B. Johansson & Anders Eklund & Jan Malm & Göran Stemme & Niclas Roxhed Biomed Microdevices, 2014.

*Primary Examiner* — Philip R Wiest
(74) *Attorney, Agent, or Firm* — Gabriela B. Tomescu, Esq.; Bergenstråhle & Partners AB

(57) ABSTRACT

The disclosure relates to a cerebrospinal fluid (CSF) shunt for treatment of hydrocephalus, comprising a valve having an inlet port and an outlet port, which ports are for draining CSF, and a control port for regulating the drainage of CSF through the valve according to a hydrostatic pressure provided to the control port, which hydrostatic pressure is dependent on the body position of the patient. The disclosure further relates to a method for treatment of hydrocephalus comprising regulating drainage of CSF based on a hydrostatic pressure that is dependent on the body position of the patient.

12 Claims, 5 Drawing Sheets

(58) Field of Classification Search
USPC .............................................................. 604/9
See application file for complete search history.

(56) References Cited

U.S. PATENT DOCUMENTS

| | | | | |
|---|---|---|---|---|
| 9,498,379 | B2* | 11/2016 | Rickard | .............. A61F 9/00781 |
| 2003/0139699 | A1* | 7/2003 | Rosenberg | .......... A61M 27/006 |
| | | | | 604/9 |
| 2005/0038371 | A1 | 2/2005 | Reich et al. | |
| 2014/0024995 | A1* | 1/2014 | Seaver | ................ A61M 27/006 |
| | | | | 604/10 |

FOREIGN PATENT DOCUMENTS

| | | | |
|---|---|---|---|
| EP | 1331019 | A2 | 7/2003 |
| JP | S62-002948 | A | 1/1987 |
| JP | 2003250881 | A | 9/2009 |
| WO | 98/02202 | A | 1/1998 |

* cited by examiner

CEREBROSPINAL FLUID SHUNT FOR TREATMENT OF HYDROCEPHALUS

This application is a continuation of PCT Application No. PCT/SE2013/051140, filed Oct. 10, 2013, which claims priority to Application No. SE 1200588-0, filed Oct. 1, 2012, the entire contents of each of which are hereby incorporated by reference.

TECHNICAL FIELD

The present invention relates generally to an implantable cerebrospinal fluid (CSF) shunt for treatment of hydrocephalus, and a method for regulating the drainage of CSF according to body position of the patient.

BACKGROUND ART

CSF is a water like body fluid that occupies the space between the brain and the skull and also the spaces (ventricles) inside the brain as well as in the spinal canal. It is produced in the brain to provide cushion and a homeostatic environment as well as immunological protection. CSF is produced at a rate of 0.3-0.6 ml/min and the pressure is kept at equilibrium by absorption with the same flow rate. However, when diagnosed for Hydrocephalus, there is a disturbance in the CSF circulating system that causes the ventricles of the brain to enlarge and in some cases the pressure to be increased above normal values, for instance by reduced absorption or by CSF-flow obstruction. The disturbed CSF system may lead to symptoms such as headache, unconsciousness, gait and balance disturbances and cognitive decline.

The treatment of hydrocephalus generally implies a surgical operation where a shunt system with catheters and valve is placed with an inlet in the intracranial space and an outlet in a place in the body where the fluid can be resorbed, most often the abdominal cavity (ventriculo-peritoneal, VP CSF shunt). A previously known shunt is disclosed in U.S. Pat. No. 4,861,331.

A shortcoming with the known solution is that the drainage will be dependent on the body position, e.g. if the patient is in an upright position or is lying down. Thus the drainage may be too low or too large due to changes in the body position.

SUMMARY OF INVENTION

An object of the present invention is to reduce the above shortcomings and to provide an improved CSF shunt for treatment of hydrocephalus.

Thus the invention relates to a CSF shunt for treatment of hydrocephalus, comprising a valve having an inlet port and an outlet port, which ports are for draining CSF, and a control port for regulating the drainage of CSF through the valve according to a hydrostatic pressure provided to the control port, which hydrostatic pressure is dependent on the body position of the patient.

By providing a valve with a control port and regulating the drainage of CSF through the valve according to a hydrostatic pressure provided to the control port, the hydrostatic pressure being dependent on the body position of the patient, the shunt reduces the risk of over or under drainage of the CSF as dependent on if the patient is in an upright position or is lying down.

The hydrostatic pressure may further be dependent on other internal/external pressure variations. Thus influences from other external or internal pressures such as increased pressure in abdomen may be reduced.

The valve may preferably be a miniaturized valve, having small dimensions, in the order of millimeters, suitable for implantation. The size of the valve may be less than 10×10×5 mm, or less than 7×7×2 mm. The shunt may be a MEMS-based CSF shunt, comprising a MEMS-based valve. MEMS is short for microelectromechanical systems and is defined to encompass devices formed by micromachining techniques. Micromachining is defined to include fabrication techniques with a level of accuracy in the range below 10 µm, preferably in the range below 1 µm. Micromachining may include one or more of lithography, wet etching, dry etching (such as deep reactive ion etching, DRIE) etc, but may further include one or more of electron or ion bean machining, plasma beam machining, laser machining, electro discharge machining, micromilling, micromolding, microreplication in a polymer, micro solid freeform fabrication, micro stereo lithography, electroplating and the like. Micromachining allows for a miniaturised device that may be batch fabricated at very high dimensional accuracy and produced at a reduced cost.

The shunt may be configured such that an increasing pressure at the control port provides an increasing opening pressure of the valve for drainage of CSF.

Thus the shunt may be arranged in the body of a patient, having the valve easily accessible e.g. in the chest region, while the drainage of CSF from e.g. a ventricular space in may be compensated for hydrostatic gravity effects.

The valve may comprise a membrane separating an inlet and/or outlet space of the valve, connected to the inlet port and/or the outlet port, from a control space of the valve, connected to the control port, and wherein the membrane is arranged such that a pressure difference over the inlet and/or outlet space and the control space regulates the opening pressure of the valve for drainage of CSF from the inlet port to the outlet port of the valve.

Thereby the valve may in a simple way be arranged to self-regulate the drainage of CSF dependent on body position of the patient.

The valve may be configured such that a portion of the membrane in pressure-transmitting contact with the inlet port is larger or much larger than a portion of the membrane in pressure-transmitting contact with the outlet port.

The shunt may further comprise a ventricular catheter for connection to a ventricular space in the patient and connected to the inlet port of the valve.

Thus the drainage of CSF from a ventricular space may be regulated.

The shunt may further comprise a distal catheter for connection to an abdominal space, or to the right atrium of the patient, and connected to the outlet port of the valve.

Thus the CSF may be drained to a space in the body suitable for resorbtion.

The shunt may further comprise a hydrostatic pressure device connected to the control port. The hydrostatic pressure may be created by a liquid column in the hydrostatic pressure device.

Thus the regulation of drainage with respect to body position may be achieved by the hydrostatic pressure from the liquid column in the hydrostatic pressure device.

The hydrostatic pressure device may comprise a liquid filled compensation catheter defining the liquid column, wherein a first end of the catheter, defining a first end of the liquid column, is connected to the control port.

Thus the liquid column may be achieved in a simple catheter system suitable for implantation in the body of a patient.

A second end of the compensation catheter, defining a second end of the liquid column, may comprise a hydrostatic pressure transmitting membrane for exposure to ambient pressure.

Thus the second end of the compensation catheter may be located in the body such that it is exposed to ambient pressure, thus compensating purely for hydrostatic pressure along the compensation catheter. Further, since a miniaturized and/or MEMS-based valve only requires a minimum of fluid flow through the control port to regulate the drainage of CSF, the compensation catheter may be adapted to transmit substantially only hydrostatic pressure. Further, the valve may be implanted at different locations in the body, while still regulating the drainage of CSF according to body position of the patient and with respect to the ambient pressure.

Thus the positioning of the hydrostatic pressure transmitting membrane of the compensation catheter with respect to the location of the ventricular catheter in the ventricular space may be chosen to mimic a normally functional physiological system. The position of the hydrostatic pressure transmitting membrane may be selected to be close to the neck region of the patient.

The hydrostatic pressure transmitting membrane may be comprised in a pressure transmitting bladder.

Thus the hydrostatic pressure transmitting device, e.g. the compensation catheter, may be adapted to transmit hydrostatic pressure while transmitting a limited flow to the miniaturized and/or MEMS-based valve.

The control port may be used to select a reference level for a hydrostatic indifference point by connecting the control port, via the hydrostatic pressure transmitting device, at a desired level in the body. The level in the body may e.g. correspond to the level of the neck. This would result in an about 10 cm $H_2O$ positive ICP in lying down while it would yield a slightly negative ICP in upright position.

The level of the valve in the body may not influence the opening pressure of the valve system since the hydrostatic component on the control port and the inlet port with respect to placement of the hydrostatic pressure transmitting device will effectively cancel out each other. This leaves the level of the hydrostatic pressure transmitting device as the control level for the ICP regulation. Thus a shunt system may be provided that is independent of where the valve is placed in the body, and that controls the opening pressure of the valve to correspond to a physiological level chosen through the level of placement of the hydrostatic pressure transmitting device.

The compensation catheter and the ventricular catheter may be formed as a double catheter to extend alongside one another.

Thus a portion of the hydrostatic pressure in the ventricular catheter may be compensated for by regulating the drainage by the hydrostatic pressure in the coextending compensation catheter of the double catheter.

The valve may be configured such that if equal hydrostatic pressures are applied to the inlet port and the control port they will cancel each other.

Thus the opening pressure of the shunt may be adopted different conditions, such as individual patients, by careful selection of the location of the hydrostatic pressure device connected to the control port.

The regulation of the drainage is preferably passive and thus self-regulating. Thus the shunt may be formed as a simple and relatively inexpensive unit independent on any active control, avoiding the need for electronics, power sources and the like.

The valve may be formed by silicon micromachining. Thus the valve may be precisely defined, batch fabricated at a reduced cost and in a mechanically robust material suitable for long term implantation in the body of a patient.

The valve may be pressure balanced and the control port connected to a hydrostatic pressure generating catheter such that a pressure on the control port will balance against the inlet pressure causing a shift in the pressure to flow relationship in fluid flow from the inlet to the outlet port.

Thus the invention may alternatively relate to a MEMS-based passive shunt with adaptive flow characteristics for treatment of hydrocephalus comprising a pressure balanced valve having an inlet, an outlet and a control port connected to a hydrostatic pressure generating catheter such that a pressure on the control port will balance against the inlet pressure causing a shift in the pressure to flow relationship in fluid flow from the inlet to the outlet port.

The control port may be arranged to control the flow characteristics of the valve such that to shift the flow to pressure relationship between the inlet and outlet ports by means of a pressure bias on the control port, and the shunt may comprise a catheter system comprising:
  a ventricular catheter for connection to a ventricular space in the patient, and connected to the inlet port of the valve,
  a distal catheter for connection to an abdominal space in the patient, and connected to the outlet port of the valve, and
  a hydrostatic pressure catheter comprising a hydrostatic pressure device and connected to the control port of the valve to provide change in hydrostatic pressure as bias to the control port, such that to adapt the rate of drainage to the body position of the patient.

Thus the invention may alternatively relate to an implantable MEMS-based passive shunt comprising a valve having an inlet port, an outlet port and a control port. The control port is arranged to control the flow characteristics of the valve such that to shift the flow to pressure relationship between the inlet and outlet ports by means of a pressure bias on the control port. The shunt further comprises a catheter system comprising a ventricular catheter for connection to a ventricular space in the patient, and connected to the inlet port of the valve, a distal catheter for connection to an abdominal space in the patient, and connected to the outlet port of the valve, and a hydrostatic pressure catheter comprising a hydrostatic pressure sensing device and connected to the control port of the valve to provide change in hydrostatic pressure as bias to the control port, such that to adapt the rate of drainage to the body position of the patient.

The invention further relates to the use of a CSF shunt as disclosed herein for treatment of hydrocephalus.

The invention further relates to a method for treatment of hydrocephalus comprising regulating drainage of cerebrospinal fluid (CSF) based on a hydrostatic pressure that is dependent on the body position of the patient.

The method may further comprise providing a CSF shunt as disclosed herein for regulating the drainage of CSF.

BRIEF DESCRIPTION OF DRAWINGS

The invention is now described, by way of example, with reference to the accompanying drawings, in which.

DESCRIPTION OF EMBODIMENTS

In the following, various embodiments of the shunt will be described in further detail.

Figure 1:
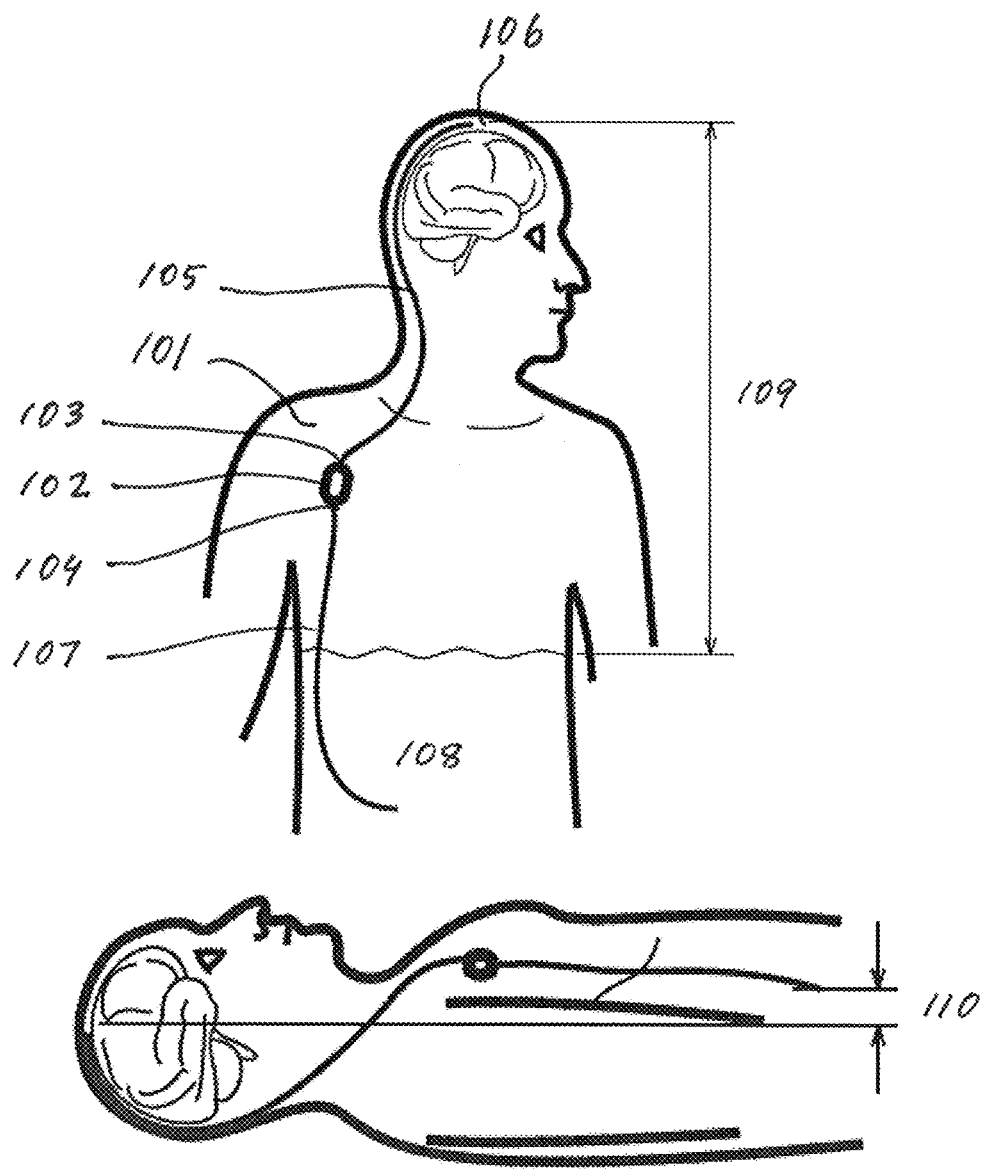
FIG. 1 shows a conventional shunt for drainage of CSF.

Existing hydrocephalus shunts 101 as shown in FIG. 1 comprise a valve 102 provided with two flow ports, one inlet 103 and one outlet 104. A ventricular catheter 105 is connected to the inlet and extends to a ventricular space 106 in the patient. A distal catheter 107 is connected to the outlet and extends to the abdomen 108 of the patient. The valve of the shunt system is configured to open at a predefined over pressure in order to drain CSF from the ventricular space to the abdomen for resorbtion. However, due to effects of gravity the pressure of the CSF at the level of the valve will be significantly affected by the body position of the patient. In FIG. 1, the hydrostatic pressure difference is illustrated for an upright position 109 and a lying position 110.

Given that the hydrostatic pressure difference between inlet and outlet in a traditional shunt system may be up to 50 cm $H_2O$ in humans depending on body position and a preferred regulated posture effect on intracranial CSF pressure is a reduction in the order of 10-15 cm $H_2O$, it becomes clear that it is essential to compensate for the gravity effect to achieve accurate drainage. Both to optimize clinical improvement but also to reduce the risk of adverse events such as subdural hematomas from over drainage.

The present disclosure thus presents an implantable micro fabricated hydrocephalus shunt that can adapt its rate of drainage according to the current body position of the patient. This is achieved by utilizing the change in hydrostatic pressure as a bias in the shunt. Thus the shunt may overcome problems with over and under drainage due to changing body position.

Figure 2:
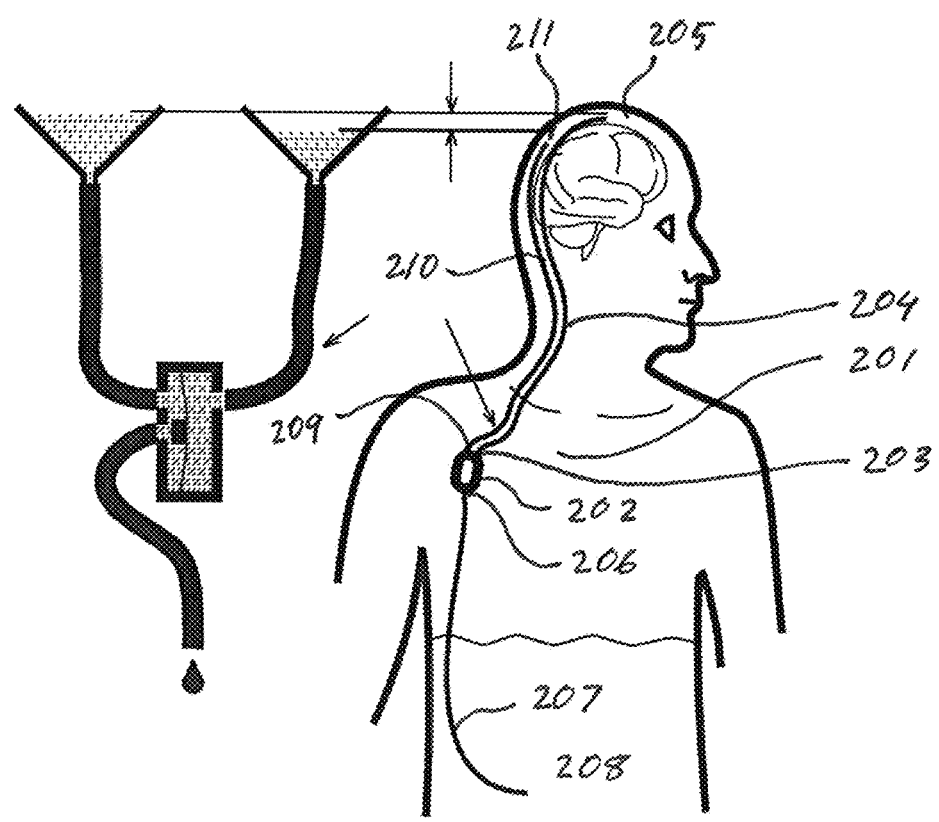
FIG. 2 shows a shunt according to the present disclosure.

In FIG. 2, one example of a shunt 201 according to the present disclosure is shown. The shunt comprises a valve 202 with an inlet port 203, connected to a ventricular catheter 204 extending to a ventricular space 205 of the patient, and an outlet port 206 connected to a distal catheter 207 extending to an abdominal space 208 of the patient. and the valve further comprises a third port, the control port 209, which utilizes hydrostatic pressure to control the flow characteristics of the valve and adapt CSF drainage according to body position. The construction of the valve will be described in further detail in relation to FIG. 4.

A compensation catheter 210 filled with a suitable liquid, such as water, may be used as a hydrostatic pressure device that will then provide the necessary bias to the control port. The liquid may alternatively be a liquid more dense than water to increase the hydrostatic pressure generated by the liquid column formed. The pressure compensating catheter may be a closed compartment filled with water and sealed by a flexible bladder, or a membrane 211, enabling a small amount of fluid to move between the catheter and the valve. The valve utilizes the hydrostatic pressure received from this catheter to balance against the hydrostatic pressure bias on the regular inlet port used for draining CSF.

If two equal hydrostatic pressures are applied on the valve, one on the inlet and one on the control port, they will therefore successfully cancel each other and the shunt system will not be affected by gravity.

Figure 3A:
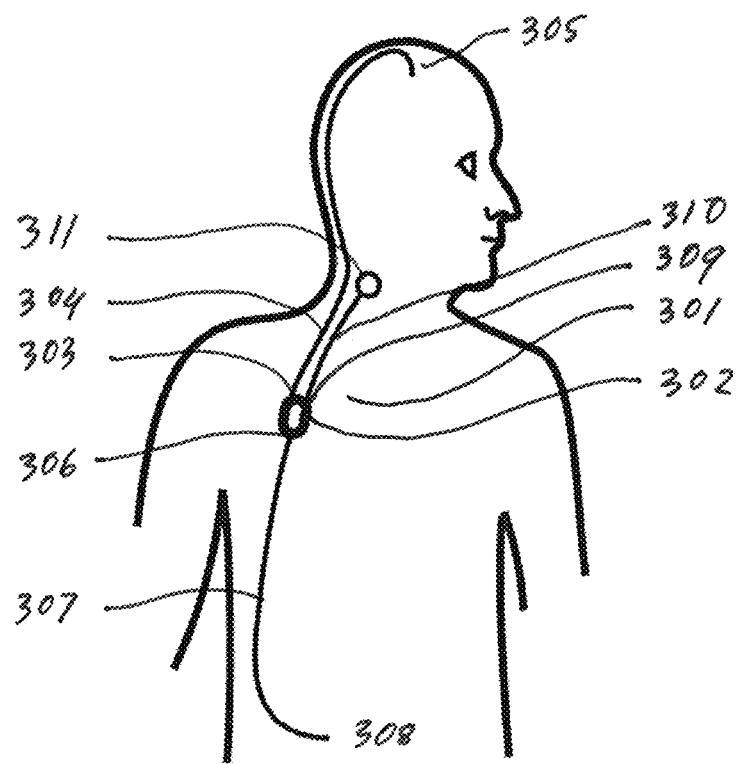
FIGS. 3a and b shows other shunts according to the present disclosure.

In FIG. 3a another example of a shunt 301 is shown. The shunt comprises a valve 302 implanted in the chest region of a patient. The valve is provided with an inlet port 303, connected to a ventricular catheter 304 extending to a ventricular space 305 of the patient, and an outlet port 306 connected to a distal catheter 307 extending to an abdominal space 308 of the patient. The valve further comprises a control port 309, which utilizes hydrostatic pressure to control the flow characteristics of the valve. The control port is connected to a hydrostatic pressure device in the form of a liquid filled compensation catheter 310. A second end of the compensation catheter comprises a pressure transmitting bladder 311 comprising a membrane. The pressure transmitting bladder is connected to the ambient pressure at the neck region of the patient.

Figure 3B:
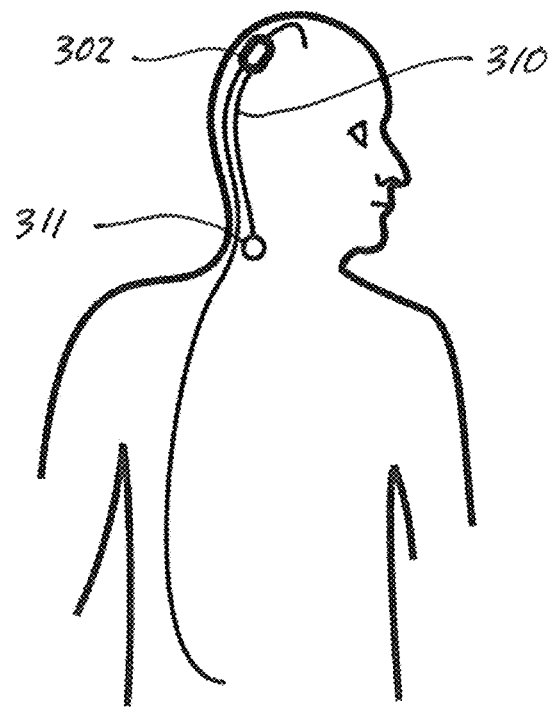

In FIG. 3b yet another example of a shunt is shown. The valve 302 is implanted in the skull of the patient, closely connected to a ventricular catheter extending to a ventricular space of the patient. The control port is connected to a hydrostatic pressure device in the form of a liquid filled compensation catheter 310. A second end of the compensation catheter comprises a pressure transmitting bladder 311 comprising a membrane. As in previous example the pressure transmitting bladder is connected to the ambient pressure at the neck region of the patient.

Thus CSF may be drained by the shunt such that the ICP is reduced to a level corresponding to the ambient pressure when lying down, and to a slight under pressure compared to ambient pressure when in an upright position. This corresponds to normally functional physiological conditions.

Figure 4A:
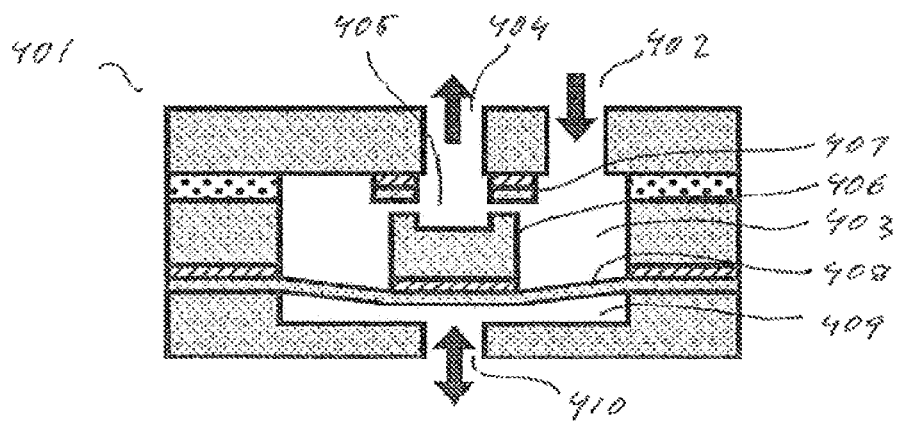
FIGS. 4a and b shows a valve in cross-sectional view and partly cut-away perspective view.
Figure 4B:
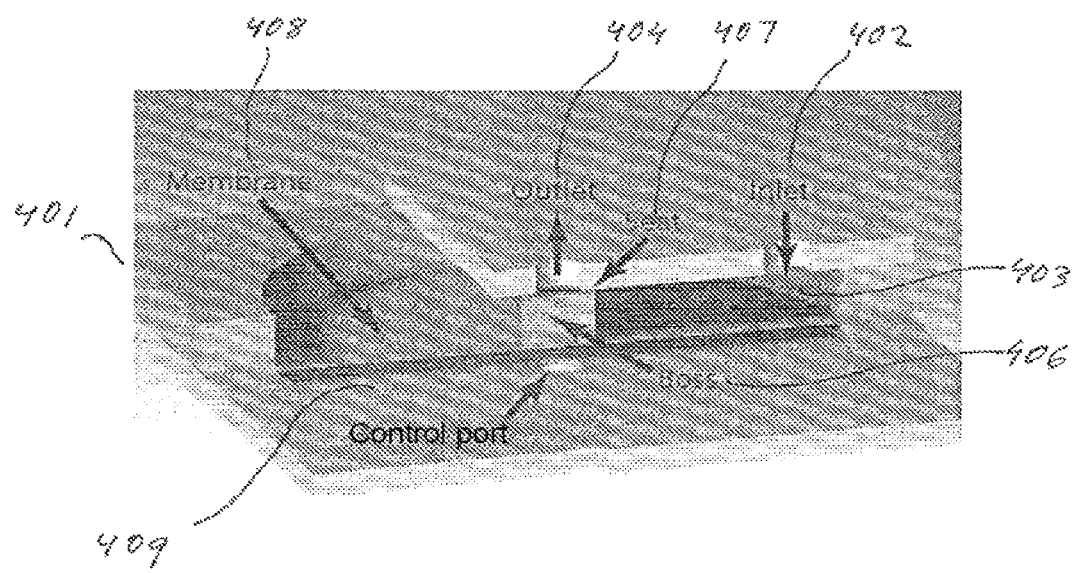

FIGS. 4a and 4b show examples of a valve 401 of the shunt system. The valve comprises an inlet port 402 connected to an inlet space 403. An outlet port 404 connected to an outlet space 405 sealed from the inlet space by means of a valve boss 406 and seat 407. The boss is supported by a membrane 408 of the valve. The area of the boss is much smaller than the area of the membrane. The membrane separates the inlet space from a control space connected to the control port 410. As pressure on the inlet port 402 increases, the membrane 408 will deflect and an opening is created such that fluid flow from the inlet port to the outlet port 404 is enabled. A pressure on the control port 410 will balance against the inlet pressure causing a shift in the pressure to flow ratio. A positive or negative pressure bias on the control port relative the inlet port may thus shift the flow to pressure relationship of the valve.

A MEMS-based valve is fabricated from three sandwiched silicon wafers and comprises three ports for connecting fluids. The middle wafer in the stack is an SOI wafer used to form a pressure balanced membrane, while the outer wafers are used to form the fluidic ports and a cavity to enable membrane movement, as illustrated in FIG. 4. As pressure on the inlet port increases, the membrane will deflect and an opening is created such that fluid flow from the inlet port to the outlet port is enabled. Since the area of the valve boss is much smaller than the membrane area, the effective membrane area seen by the inlet port pressure pin and the control port pressure $p_{compensate}$ are approximately the same. Hence a certain pressure applied on the control port will act as a reduction by the same amount on the inlet port:

$$p_{membrane} = p_{in} - p_{compensate}$$

where $p_{membrane}$ is the effective net pressure acting on the membrane.

By connecting the valve to a compensation pressure catheter with a certain length as shown in FIG. 2 and FIG. 3, the shunt system enables the unique feature to set the drainage level for lying and standing body position independently of each other by changing the geometry of the valve and the length of the compensation pressure catheter, respectively. For example, if the geometry of the valve is defined such that the CSF will be drained until the intracranial pressure (ICP) is reduced to 10 cm H2O in lying position and the length of the compensating water column in the compensation pressure catheter ($h_{compensate}$) is 30 cm, the effective input pressure on the membrane in standing position will be reduced by the same pressure as given by the compensation pressure catheter:

$$p_{membrane} = p_{in} - \rho g h_{compensate} =$$
$$ICP + \rho g h_{standing} - \rho g h_{compensate} \approx (10 + 50 - 30) \text{ cm H}_2\text{O} =$$
$$30 \text{ cm H}_2\text{O}$$

where ρ is the density of CSF, g is the gravity and $h_{standing}$ is the hydrostatic height difference in standing position.

In lying position the pressure will be:

$$p_{membrane} = p_{in} - \rho g h_{compensate} =$$
$$ICP + \rho g h_{lying} - \rho g h_{compensate} \approx (10 + 0 - 0) \text{ cm H}_2\text{O} \approx 10 \text{ cm H}_2\text{O}$$

where $h_{laying}$ is the hydrostatic height difference in lying position. Hence, when standing up, the effective pressure on the membrane will increase with a bias of 20 cm H2O causing increased CSF drainage. Because CSF production is approximately constant at 0.3-0.6 ml/min, the elevated drainage will continue only until the ICP has reduced by 20 cm H2O, compensating for the added bias and returning to the same flow/pressure equilibrium as in the lying position. In healthy individuals it expected that ICP is reduced from approximately 10 cm $H_2O$ in lying position to –10 cm $H_2O$ in upright position, thus the effect of body position on the ICP may be reduced to levels seen in healthy persons.

Experiments with shunts according to the present disclosure showed a flow rate of approximately 1.1 ml/min at a pressure of 1500 Pa, 0.7 ml/min at 1000 pa and 0.3 ml/min at 500 Pa. This indicates that for the given production rate of CSF the resulting pressure difference on the shunt will be approximately 500-900 Pa. The abdominal counter pressure at the distal catheter will add to this pressure difference so that the final CSF pressure in the subarachnoid space and ventricles will be higher, meeting the required pressure/flow window for treating hydrocephalus.

Figure 5:
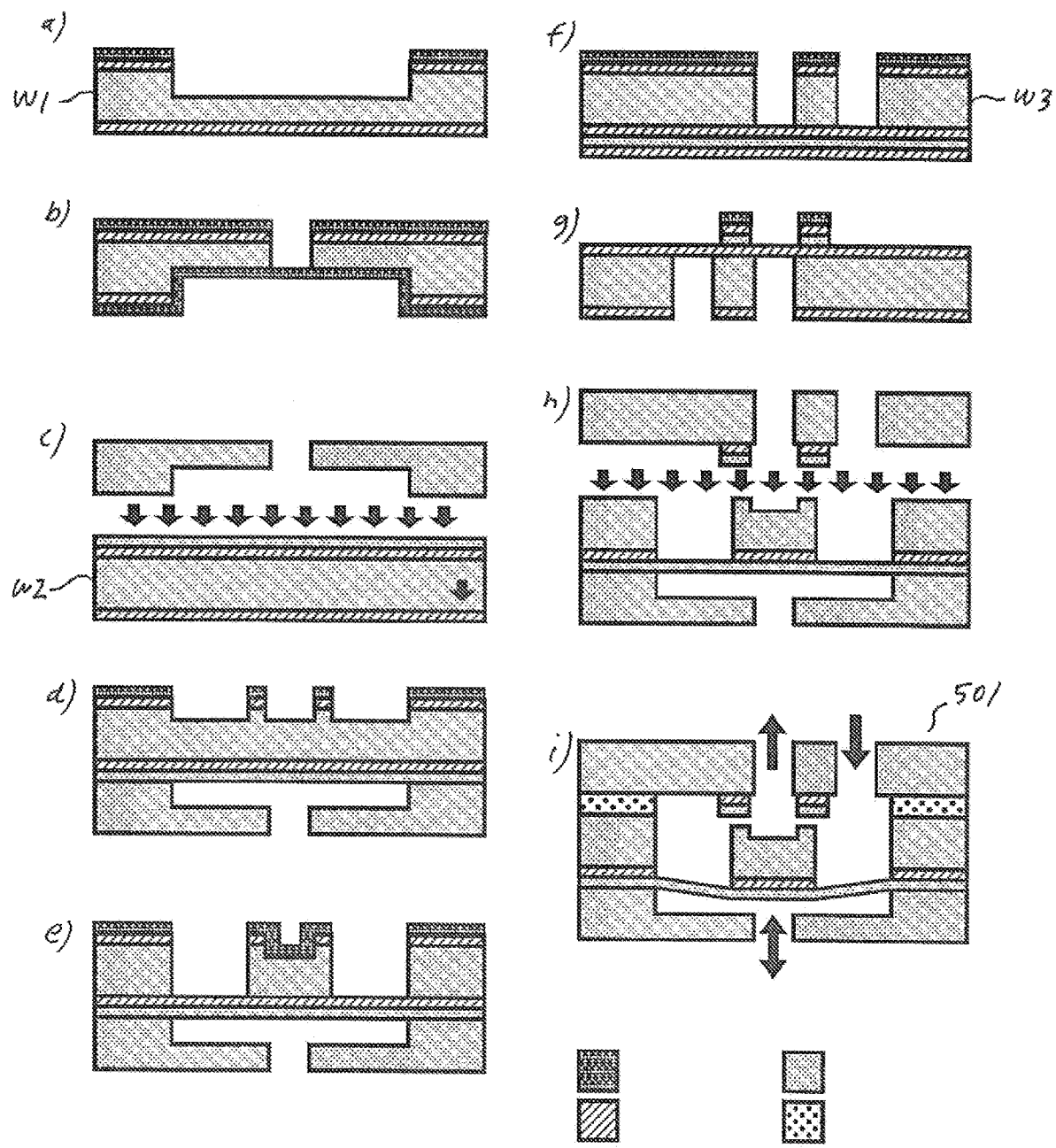
FIG. 5 shows an example of fabrication of a valve for a shunt according to the present disclosure.

An example of a fabrication process of MEMS-based valves 501 of the shunt according to the present disclosure is shown in FIG. 5. Three wafers, W1 (silicon wafer 300 μm thick), W2 (SOI wafer 525/10 μm thick) and W3 (silicon wafer 300 μm thick) were first oxidized to 1 μm thickness by wet thermal oxidation at 1100° C.

Wafer W1 was then spin coated with photo resist (PR) (Shipley 720-1.2) and patterned by standard UV-lithography. The oxide was then etched by reactive ion etching (RIE) and 180 μm deep cavities were etched by deep RIE (STS ICP Multiplex ASE) to enable membrane movement and forming the control space (FIG. 5*a*). Before etching the control ports from the other side of wafer W1, the photo resist mask was removed by O2 plasma (Tepla Model 300) and an etch stop layer was created by spray coating with 1:2:10 AZ9260 PR, RER600 edge bead remover and methyl ethyl ketone (MEK) (FIG. 5*b*).

Prior to bonding wafer W1 to SOI wafer W2 (FIG. 5*c*), wafer W1 was stripped from photo resist (O2 plasma) and oxide (BHF) while wafer W2 was stripped from oxide (BHF) on the device layer, then both wafers were cleaned for 2 minutes in $H_2O_2$:$H_2SO_4$ 1:4 with 100 ppm HF added. The addition of HF to the cleaning solution was made to create competitive chemical processes of oxidation and etching, causing smoothening of the surface at an atomic scale which increases bond strength.

The cleaning step was finalized by bubbling in deionized water for 10 minutes and then >5 minutes in a rinse and dryer. Fusion bonding of W1 and W2 was then performed in a substrate bonder (Suss Microtec CB8) at vacuum and room temperature with 3 kN bond force for 1 minute followed by $N_2$ anneal at 1100° C. for 2 hours.

The bonded wafer stack W1/W2 was then patterned and etched in two steps to fabricate the CSF valve boss and seat, (FIG. 5*d-e*). Wafer W3 is then patterned and etched to fabricate 0.4 mm diameter inlet and outlet ports (FIG. 4*f*). A valve seat is thereafter etched in the device layer of the wafer W3. After removing the photo resist the wafer stack W1/W2 and wafer W3 were diced (Disco DAD320) and final assembly was made on chip level.

The chip parts were aligned under microscope (FIG. 5*h*) and low viscosity glue (Loctite 420) was applied at the chip stack perimeter resulting in capillary filling of the space between the W1/W2 and W3 chips (FIG. 5*i*). The diameter of the membrane may be about 5.6 mm and the fabricated valve may measure 6×6×1.1 $mm^3$, a size well suited for neurosurgical implants.

The invention claimed is:

1. A cerebrospinal fluid (CSF) shunt for treatment of hydrocephalus, comprising a valve having:
   an inlet port connected to a ventricular catheter for connection to a ventricular space in the patient;
   an outlet port, the inlet and the outlet ports are for draining CSF; and
   a control port for regulating the drainage of CSF through the valve according to a hydrostatic pressure dependent on the body position of the patient and provided to the control port by a hydrostatic pressure device comprising a liquid filled compensation catheter defining a liquid column to create a hydrostatic pressure dependent on the body position of the patient, wherein a first end of said compensation catheter, defining a first end of the liquid column, which is connected to said control port and a second end, defining a second end of the liquid column, which comprises a hydrostatic pressure transmitting means configured to be exposed to ambient air, and
wherein,
   the valve comprises a membrane separating an inlet and an outlet space of the valve, connected to the inlet port and the outlet port, from a control space of the valve, connected to the control port, and
   the membrane is arranged such that a pressure difference over the inlet space and the control space regulates the opening of the valve for drainage of CSF from the inlet port to the outlet port of the valve and wherein is the valve is configured so that if equal hydrostatic pressures are applied to the inlet port and the control port they will cancel each other;

the valve comprises a valve boss supported by the membrane and a corresponding seat configured to cooperate to open and close the outlet port depending on the balance between the inlet space pressure and the control space pressure;

the area of said valve boss is smaller than the membrane area; and the pressure of the CSF in the inlet space is exerted on substantially the full membrane area when the valve is both opened and closed.

2. The shunt according to claim 1 configured such that an increasing pressure at the control port provides an increasing opening pressure of the valve for drainage of CSF.

3. The shunt according to claim 1, further comprising a distal catheter for connection to an abdominal space, or to a right atrium of the patient, and connected to the outlet port of the valve.

4. The shunt according to claim 1, wherein the hydrostatic pressure transmitting means comprises a membrane, comprised in a pressure transmitting bladder.

5. The shunt according to claim 1, wherein the compensation catheter and the ventricular catheter are formed as a double catheter to extend alongside one another.

6. The shunt according to claim 1, wherein the valve is formed by silicon micromachining.

7. The shunt according to claim 1, wherein the shunt is MEMS-based, and wherein the valve is pressure balanced and the control port connected to the hydrostatic pressure device such that a pressure on the control port will balance against the inlet pressure causing a shift in the pressure to flow relationship in fluid flow from the inlet to the outlet port.

8. The shunt according to claim 1, wherein the shunt is implantable and MEMS-based, and wherein the control port is arranged to control flow characteristics of the valve such that to shift the flow to pressure relationship between the inlet and outlet ports by means of a pressure bias on the control port, and a catheter system comprising the ventricular catheter for connection to a ventricular space in the patient, and connected to the inlet port of the valve, a distal catheter for connection to an abdominal space in the patient, and connected to the outlet port of the valve, and the hydrostatic pressure device connected to the control port of the valve to provide change in hydrostatic pressure as bias to the control port, so as to adapt the rate of drainage to the body position of the patient.

9. A method of adapting CSF drainage according to a patient's body position comprising implanting a microelectromechanical systems (MEMS)-based CSF shunt according to claim 8, comprising a MEMS-based valve; and using the hydrostatic pressure from the control port to balance against the hydrostatic pressure bias from the inlet port to control flow characteristics of the valve.

10. A method for treatment of hydrocephalus comprising regulating a drainage of cerebrospinal fluid (CSF) based on a hydrostatic pressure that is dependent on a patient's body position, comprising providing a CSF shunt according to claim 1 for regulating the drainage of CSF.

11. The shunt according to claim 1, comprising a valve boss supported by the membrane and a corresponding seat configured to cooperate to open and close the outlet port depending on the balance between the inlet port pressure and the control port pressure.

12. The shunt according to claim 11, wherein the area of the valve boss is smaller than the membrane area.

* * * * *